(12) United States Patent
Petzoldt et al.

(10) Patent No.: US 7,927,555 B2
(45) Date of Patent: Apr. 19, 2011

(54) CHARGING OF A REACTOR

(75) Inventors: Jochen Petzoldt, Weisenheim am Berg (DE); Ulrich Cremer, Mannheim (DE); Martin Dieterle, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1190 days.

(21) Appl. No.: 11/369,042

(22) Filed: Mar. 7, 2006

(65) Prior Publication Data

US 2006/0201573 A1    Sep. 14, 2006

Related U.S. Application Data

(60) Provisional application No. 60/659,074, filed on Mar. 8, 2005.

(30) Foreign Application Priority Data

Mar. 8, 2005  (DE) .................... 10 2005 010 645

(51) Int. Cl.
    *B01J 8/06*    (2006.01)
    *C07C 57/02*   (2006.01)
    *C07C 47/00*   (2006.01)

(52) U.S. Cl. .................. 422/187; 562/598; 568/420

(58) Field of Classification Search .............. 562/598; 568/420; 422/187
    See application file for complete search history.

(56) References Cited

U.S. PATENT DOCUMENTS

| | | | |
|---|---|---|---|
| 3,464,930 A * | 9/1969 | Goehre et al. ............. 502/309 |
| 3,608,751 A | 9/1971 | Hundtofte | |
| 3,749,258 A | 7/1973 | James | |
| 3,799,886 A | 3/1974 | Felice et al. | |
| 3,956,377 A | 5/1976 | Dolhyj et al. | |
| 4,036,783 A | 7/1977 | Blechschmitt et al. | |
| 4,259,211 A | 3/1981 | Krabetz et al. | |
| 4,297,247 A | 10/1981 | Krabetz et al. | |
| 4,305,843 A | 12/1981 | Krabetz et al. | |
| 4,402,349 A | 9/1983 | Engert et al. | |
| 4,438,217 A | 3/1984 | Takata et al. | |
| 4,461,327 A | 7/1984 | Magin et al. | |
| 4,522,671 A | 6/1985 | Gruenwald et al. | |
| 4,537,874 A | 8/1985 | Sato et al. | |
| 5,677,261 A * | 10/1997 | Tenten et al. ............. 502/439 |
| 5,910,608 A | 6/1999 | Tenten et al. | |
| 6,288,273 B1 | 9/2001 | Heidemann et al. | |
| 6,528,683 B1 | 3/2003 | Heidemann et al. | |
| 2004/0245681 A1 | 12/2004 | Dieterle et al. | |
| 2004/0249183 A1 | 12/2004 | Dieterle et al. | |
| 2004/0261898 A1 | 12/2004 | Goemans et al. | |

FOREIGN PATENT DOCUMENTS

| | | |
|---|---|---|
| DE | 235151 | 6/1911 |
| DE | 16 42 921 | 5/1971 |
| DE | 20 25 430 | 12/1971 |
| DE | 21 06 796 | 8/1972 |
| DE | 25 26 238 | 1/1976 |
| DE | 25 10 994 | 9/1976 |
| DE | 25 11 411 | 9/1976 |
| DE | 26 26 887 | 12/1977 |
| DE | 28 49 664 | 6/1980 |
| DE | 29 06 670 | 10/1980 |
| DE | 29 09 671 | 10/1980 |
| DE | 198 24 532 A 1 | 12/1999 |
| DE | 199 34 324 A 1 | 9/2000 |
| DE | 102 50 022 A1 | 5/2004 |
| DE | 103 60 057 A1 | 7/2004 |
| DE | 103 60 058 A1 | 7/2004 |
| DE | 103 37 998 A1 | 3/2005 |
| EP | 0 041 144 A1 | 12/1981 |
| EP | 0 037 492 B1 | 10/1984 |
| EP | 0 293 859 B1 | 1/1992 |
| EP | 0 286 448 B2 | 9/1993 |
| EP | 0 548 999 B1 | 5/1996 |
| EP | 0 714 700 A2 | 6/1996 |
| EP | 1 466 883 A1 | 10/2004 |
| GB | 896786 | 5/1962 |
| GB | 1 203 321 | 8/1970 |
| GB | 1331423 | 9/1973 |
| GB | 1346 943 | 2/1974 |
| JP | 09-141084 | * 3/1997 |
| WO | WO 98/37967 | 9/1998 |

OTHER PUBLICATIONS

Simon et al, Zeitschrift für anorganische und allgemeine Chemie, (1963) vol. 323, pp. 160-169 Certified English Translation (German version submitted Aug. 17, 2010).

Simon et al, Zeitschrift für anorganische and allgemeine Chemie, (1963) vol. 323, pp. 160-169.

* cited by examiner

*Primary Examiner* — Taylor Victor Oh

(74) *Attorney, Agent, or Firm* — Oblon, Spivak, McClelland, Maier & Neustadt, L.L.P.

(57) ABSTRACT

The present invention relates to a process for charging a reactor with a catalyst, to the resulting charged reactors, and to the use thereof for carrying out catalytic gas phase reactions.

29 Claims, No Drawings

CHARGING OF A REACTOR

The present invention relates to a process for charging a reactor with a multielement oxide catalyst, to the charged reactors obtainable in this way and to the use thereof for carrying out catalytic gas phase reactions.

Reactors which are filled with catalysts serve for the performance of various catalytic gas phase reactions. The catalyst particles used either consist of one catalytically active composition which, if appropriate with use of suitable binders, is shaped by extruding, tableting or the like to give shaped bodies (known as unsupported catalysts) or they comprise at least one catalytically active composition which is applied in coating form to a generally inert support (known as coated catalysts). In general, such catalytic gas phase reactions are realized on the industrial scale in fixed bed reactors, i.e. the reaction gas mixture flows through a standing catalyst bed, and the chemical reaction proceeds during the residence time therein. Depending on the type of reaction catalyzed, it is necessary to heat the reactors externally or to surround them with a heat exchange medium, such as a salt melt, to remove heat. Therefore, catalytic gas phase reactions are in many cases appropriately carried out in catalyst-filled tubes which are frequently designed in the form of tube bundle reactors (multiple catalyst tube reactors). The tube lengths of these reactors normally extend to a few meters (a typical catalyst tube length is in the range from about 2 to 4 m) at an internal diameter in the range of a few centimeters. The catalysts used may be present in the form of spheres, rings, cylinders, cubes, cuboids or other geometric bodies whose longitudinal dimension, appropriate to the reactor tube internal diameter, is generally a few millimeters.

When catalyst particles are charged into a reactor, especially into a vertical tube, it is possible owing to the mechanical stress, depending on the side crushing strength and fracture strength of the catalysts used, that catalyst particles break up or the catalytically active composition is partly detached from the support. The fragments which form and the attrition densify the catalyst bed and lead, in the course of later operation of the tubular reactors, disadvantageously to increased pressure drops.

A multitude of documents is concerned with the preparation of particulate catalysts and their use in gas phase reactions, but without addressing the problems in the charging of the reactor.

Oxidative chemical reactions in the gas phase over unsupported catalysts based on catalytically active oxides have been described many times. U.S. Pat. No. 4,438,217 and U.S. Pat. No. 4,522,671 recommend, for example for the catalytic oxidative preparation of acrolein or methacrolein in the gas phase, the use of unsupported catalyst rings. U.S. Pat. No. 4,537,874 likewise recommends, for the catalytic oxidative preparation of $\alpha,\beta$-monoethylenically unsaturated aldehydes in the gas phase, catalyst beds composed of unsupported catalyst rings based on multimetal oxides comprising molybdenum as the main constituent.

DE-A 20 25 430 teaches a process for preparing spherical coated catalysts based on catalytically active oxide compositions and the use for catalytic gas phase oxidations, for example of indanes to anthraquinone. DE-A 16 42 921 relates to the preparation of spherical oxidic coated catalysts by spraying of a liquid comprising the oxidic active composition in dissolved or suspended form onto hot spherical support bodies and to the use of the thus obtained catalysts for the catalytic gas phase oxidation of aromatic and unsaturated hydrocarbons to carboxylic acids or their anhydrides. The teaching of DE-A 25 10 994 corresponds substantially to the teaching of DE-A 16 42 921 with the difference that it also includes annular supports. DE-A 21 06 796 discloses the preparation of coated catalysts for catalytic gas phase oxidations by spraying aqueous suspensions of the catalytically active oxidic material onto the moving support bodies. To increase the adhesion strength of the oxidic catalytically active coating on the surface of the support body, DE-A 26 26 887 recommends the incorporation of inorganic hydroxy salts into the aqueous suspension to be sprayed on. The teaching of DE-A 29 09 670 corresponds substantially to that of DE-A 26 26 887. In the former patent, the suspension medium may also be a mixture of water and alcohol. DE-A 29 09 671 describes a process for preparing coated catalysts in which the spherical support bodies are conducted periodically under two metering apparatuses arranged successively at a particular separation.

GB-1 331 423, EP-A 286 448 and EP-A 37 492 relate to processes for preparing spherical oxidic coated catalysts. EP-B 293 859 discloses a process for preparing spherical coated catalysts by employing a centrifugal flow-coating apparatus. The binders mentioned by EP-B 293 859 are water, alcohol and acetone, as well as ammonium nitrate, graphite and starch.

DE-A 25 26 238, U.S. Pat. No. 3,956,377 and DE-A 235 151 disclose processes for preparing spherical oxide coated catalysts in which the support spheres are initially moistened with water or another liquid such as petroleum ether as a binder. Subsequently, the catalytically active oxide composition is applied to the binder-moistened support material by rolling the moist support material in the pulverulent catalytically active oxide composition.

DE-A-103 60 057 and DE-A-103 60 058 describe processes for preparing catalytically active multielement oxide compositions by thermal treatment of a precursor composition in a rotary tube furnace.

WO 98/37967 describes a process for preparing coated catalysts in which a solution or a suspension which comprises a precursor compound of the catalytically active compositions is applied in coating form to the catalyst support and the supports coated in this way are subjected to a heat treatment.

DE-A-198 24 532 describes a process for preparing coated catalysts by spraying a binder-containing aqueous active composition suspension onto a support material at from 50 to 450° C. The binder used consists of a mixture of a polymer which comprises ethylenically unsaturated acid anhydrides or ethylenically unsaturated dicarboxylic acids in copolymerized form with at least one alkanolamine. The spraying of the active composition suspension onto the preheated support results in curing of the binder addition.

EP-A-714 700 describes a process for preparing a coated catalyst in which a support body is initially moistened with a liquid binder, then a layer of this catalyst composition is adhered to the surface of the support body by contacting with dry, finely divided, active oxide composition and the liquid binder is subsequently removed.

Loading apparatus for tube bundle reactors is known from DE-A-25 11 411, DE-A-28 49 664, EP-B-041 144, DE-A-199 34 324 and DE-A-102 50 022. The problems which occur owing to mechanical stress in the course of charging of the catalyst particles are not addressed in these documents.

It is also known that charging aids can be used to charge catalyst particles into reactors, for example in order to decelerate the falling rate of the catalyst particles in the course of charging. For instance, EP-A 548 999 describes a process for charging tubes in which the catalyst particles are charged along a line which has flexible brushes which extend in the transverse direction and are spaced apart from one another.

A further process for charging catalyst particles into a tube is described in U.S. Pat. No. 3,608,751. The charging aid used here is a flexible member, for example a manila line, to which inclined blades are secured.

DE-A-103 37 998 describes a process for charging a vertical tube with catalyst particles, in which a flexible elongated member is introduced into the vertical tube as a charging aid and then the catalyst particles are introduced.

However, the use of charging aids is always associated with additional complexity in the charging operation. In addition, many filling aids lead, in the case of small tubular diameters, rapidly to the blockage of the tube or to the enmeshing of the catalyst particles. In addition, catalyst fracture and attrition cannot always be prevented to the desired extent.

It is therefore an object of the present invention to provide a process by which reactors, especially those having tubes of low diameter, as are used for catalyzed gas phase reactions, can be charged effectively with prevention of catalyst fracture and attrition.

This object is achieved by a process for charging a reactor with catalyst particles which have a catalytically active multielement oxide composition at least on its surface, in which catalyst particles are provided which comprise a substance which is liquid at 20° C. and 1 atm and these catalyst particles are charged into the reactor.

It has been found that the charging of the reactor with catalyst particles which comprise a liquid substance provides catalyst charges with advantageous properties. For instance, the catalyst particles comprising such a liquid have a better mechanical stability than particles which do not comprise such a liquid. The catalyst-charged reactors obtained by the process according to the invention contain fewer fragments and/or attritus which is attributable to the mechanical stress on the catalyst in the charging operation. Thus, a less densely packed, looser bed with lower bulk density is obtained. This allows pressure drops along the catalyst charge at least to be reduced when the reactors are used. A uniform flow through the reactor and the avoidance of excessively high partial pressures of the reactants are advantageous overall for all types of catalytic gas phase reactions. For instance, lower pressure drops in the course of operation of the reactor allows compression energy to be saved, since the gas fed to the reactor has to be compressed to a lower pressure level. In addition, for example, the temperature maxima which are typically passed through in flow direction along the catalyst tubes in exothermic catalytic gas phase oxidations ("hotspots") have a reduced amplitude. This has an advantageous effect on the lifetime (onstream time) of the active composition used. In addition, a lower pressure drop in the catalyzed reaction can also lead to better space-time yields. The aforementioned advantages are exhibited especially in the charging of tube bundle reactors, which generally have at least 5000 catalyst tubes. Thus, in the charging of individual tubes, the formation of fragments and/or of attritus can be prevented substantially more readily, for example by appropriately slow charging or the use of appropriate charging aids. In industrial scale tube bundle reactors, the introduction of a new catalyst charge is, however, associated with a correspondingly long production downtime and therefore has to proceed as rapidly as possible. In addition, a pressure drop which is lower overall in the operation of a tube bundle reactor having a multitude of catalyst tubes allows distinctly more compression energy to be saved than in the case of a single-tube reactor. In addition, especially in the case of these reactors, a very uniform reaction is also desired in relation to each of the individual tubes used. However, this can only be achieved by uniform charging of each tube with the reaction gas, which has the prerequisite of substantially uniform and intact charging of all tubes with the catalyst particles.

The liquid substance used in accordance with the invention may in principle be any substance which is liquid under standard conditions (20° C. and 1 atm). These include individual liquid compounds and mixtures of two or more liquid compounds. The liquid substance may additionally comprise dissolved substances, which refer quite generally to individual dissolved compounds or mixtures of two or more dissolved compounds.

In a preferred embodiment, the catalyst particles are admixed with a liquid substance which is selected such that the particles used for charging comprise this substance in chemically unchanged form. This means that although the quantitative composition can change in the case of a substance mixture, or that the substance can enter into physical interaction with the catalyst particles, the chemical composition of the liquid substance remains unchanged when it comes into contact with the catalytically active oxide composition. When the catalyst particles are admixed with a composition which is defined in detail below, for example in the form of a binder, which comprises further components in addition to the liquid substance, the particles used for charging comprise this composition in chemically unchanged form overall. In particular, the catalyst particles are not admixed with liquid substances which comprise components having a complementary functional group capable of reaction, or with a composition comprising such substances. After the charging procedure, the chemical composition of the liquid substance may of course change, for example as a result of any drying step carried out at elevated temperatures.

Suitable liquid substances are selected from inorganic and organic liquids and mixtures thereof. These include water, nonaqueous inorganic solvents such as $HClO_4$, $HNO_3$, $H_2SO_4$, etc., organic solvents such as monohydric alcohols (e.g. methanol, ethanol, n-propanol, isopropanol, butanols, pentanols, cyclohexanol), polyols (e.g. ethylene glycol, glycerol), ethers and glycol ethers (e.g. diethyl ether, dibutyl ether, anisole, dioxane, tetrahydrofuran, mono-, di-, tri-, polyalkylene glycol ethers), ketones (e.g. acetone, butanone, cyclohexanone), esters (e.g. ethyl acetate, glycol esters), acids (e.g. acetic acid), amines, amino alcohols, amides and other nitrogen compounds (e.g. ethanolamine, diethanolamine, dimethylformamide, pyridine, N-methylpyrrolidone, acetonitrile), sulfur compounds (e.g. $CS_2$, dimethyl sulfoxide, sulfolane), nitro compounds (e.g. nitrobenzene), halohydrocarbons (e.g. dichloromethane, chloroform, tetrachloromethane, dichloroethane), hydrocarbons (e.g. benzene, petroleum ether, ligroin, pentane, hexane, heptane, cyclohexane, methylcyclohexane, decalin, aromatics such as benzene, toluene, xylene) and mixtures of the aforementioned solvents.

The liquid substance is preferably selected from water and organic solvents which have a boiling point at standard pressure (1 atm) of more than 100° C. In a specific embodiment, the liquid substance selected from water, water-miscible organic compounds which have a boiling point at standard pressure (1 atm) of more than 100° C. and mixtures thereof.

When the liquid substance used in the process according to the invention comprises dissolved inorganic or organic substances, they have a boiling point or sublimation point at standard pressure (1 atm) of more than 100° C. Suitable dissolved inorganic substances are, for example, alkali metal halides such as NaCl and KCl, alkaline earth metal halides such as $CaCl_2$ and $MgCl_2$, alkali metal and alkaline earth metal sulfates such as $Na_2SO_4$ and $CaSO_4$, alkali metal and alkaline earth metal hydroxides such as NaOH, KOH, Ca(OH)$_2$ etc. Suitable dissolved organic substances are, for example, fatty acids such as capric acid, undecanoic acid, lauric acid, tridecanoic acid, myristic acid, pentadecanoic acid, palmitic acid, margaric acid, stearic acid, nonadecanoic acid, arachic acid, behenic acid, lignoceric acid, palmitoleic acid, oleic acid, linoleic acid, linolenic acid, elaostearic acid, etc. Also suitable are mono- or oligosaccharides.

In a preferred embodiment, the liquid substance used in accordance with the invention is a substance as is typically also used to prepare the catalyst particles used to charge the reactor. This may, for example, be a binder used for catalyst preparation or a component of such a binder. In that case, as long as the binder has not been removed from the catalyst, it is generally possible to dispense with the contacting of the catalyst particles with the liquid substance before the reactor is charged. It is of course also possible to carry out the process according to the invention by contacting a catalyst which, as a result of the preparation, comprises only a small amount, if any, of liquid substance with the liquid substance by customary processes such as spraying, dipping, etc.

The liquid substance used is preferably at least one water-soluble organic compound which is liquid under standard conditions (20° C., 1 atm) and has a boiling point or sublimation point at standard pressure (1 atm) of more than 100° C. Preference is further given to using the liquid substance in the form of a composition which comprises at least one compound which is liquid under standard conditions (20° C., 1 atm) and a water-soluble organic compound which has a boiling point or sublimation point at standard pressure (1 atm) of more than 100° C. The latter statement encompasses:

- mixtures of at least one water-soluble organic compound which is liquid under standard conditions and at least one solid organic compound dissolved therein,
- mixtures of water and at least one (solid or liquid) water-soluble organic compound.

The organic component of the liquid compositions used in accordance with the invention is preferably selected from nonpolymeric components, although oligosaccharides are permissible.

Preferred liquid compositions are the solutions which are used as the liquid binder according to EP-A-714 700 and consist of from 20 to 90% by weight of water and from 10 to 80% by weight of an organic compound dissolved in water. The organic fraction of the liquid composition to be used is then preferably from 10 to 50% by weight and in particular from 20 to 30% by weight.

Suitable organic components of these liquid compositions are in particular mono- and polyhydric organic alcohols such as ethylene glycol, 1,4-butanediol, 1,6-hexanediol or glycerol, mono- or polybasic organic carboxylic acids such as propionic acid, oxalic acid, malonic acid, glutaric acid or maleic acid, amino alcohols such as ethanolamine or diethanolamine, mono- or polyfunctional organic amides such as formamide, or monosaccharides and oligosaccharides such as glucose, fructose, sucrose or lactose.

Preferred liquid substances and components of liquid compositions comprising such substances are those organic components whose boiling point or sublimation temperature at standard pressure is below the calcination temperature which has been employed to obtain the catalytically active composition. Preference is likewise given to those organic components which, in the presence of oxygen over the catalytically active oxide composition, decompose below this calcination temperature into gaseous constituents. As illustrated in detail below, it is an essential feature of the process according to the invention that the catalyst particles used to charge the reactor comprise the catalytically active composition as such and no precursor composition. To prepare the catalytically active composition, such a precursor composition is typically subjected to a thermal treatment in order to convert it to the catalytically active oxide composition (known as calcination). Typically, the calcination temperature is <500° C., frequently <400° C. and in most cases <300° C. It is generally at least 150° C., preferably at least 200° C. and in particular at least 250° C. According to the invention, particularly advantageous liquid substances are those whose boiling point at standard pressure is above 100° C., preferably above 150° C.

Examples of liquid substances which can be used advantageously are glycerol and glycerol/water mixtures.

The catalyst particles provided for the charging of the reactor preferably have a content of liquid substance of from 0.05 to 10% by weight, more preferably from 0.1 to 5% by weight, in particular from 0.5 to 2% by weight, based on their total weight.

The content of liquid substance can be determined in good approximation by determining the weight loss that the catalyst particles comprising the liquid substance undergo in the course of heating to 300° C. in air for one hour. When a finished catalyst (i.e. a catalyst in which the phase formation by calcination has been completed) is contacted with a liquid substance before the charging, the amount of liquid substance present may also be determined by simple determination of the weight difference of a sample of the catalyst. When the contacting with the liquid substance is effected in the course of the preparation of the catalyst particles, the amount of liquid substance present has to be determined from the overall mass balance of the preparation process.

In a specific embodiment, the catalyst particles provided to charge the reactor comprise the liquid substance in associated form. In the context of the present invention, an associated liquid substance refers to a liquid medium which comprises the catalyst on the basis of physical interactions such as adsorption. It is generally not a liquid phase on the catalyst surface which appears visually as such, i.e. the maximum degree of saturation of the catalyst particles is not exceeded.

According to the invention, the catalyst particles used to charge the reactor do not comprise a precursor composition but rather a catalytically active oxide composition as such. A catalytically active multielement oxide composition refers in the context of the invention to a catalytically active composition which comprises the metals (just like all other non-oxygen elements which may be present) substantially in oxidic (and not in metallic, elemental) form. The molar proportion of the nonmetals in the total amount of all non-oxygen elements of the catalytically active multielement oxide composition is at most 10 mol %, more preferably at most 5 mol %. In a specific embodiment, the catalytically active multielement oxide composition is a pure multimetal oxide composition.

The catalyst particles used in accordance with the invention have a catalytically active oxide composition which is characterized by substantially not undergoing any further weight loss in the course of heating to temperatures as are typically used in the calcination. The catalytically active composition present in the catalyst particles used in accordance with the invention, where present, together with the support material, preferably has a weight loss in the course of heating to 300° C. under air for one hour of at most 2.5% by weight, more preferably of at most 2% by weight, especially preferably of at most 1.5% by weight, based on the total weight of the catalytically active composition, and of the support where present.

Multielement oxide compositions and processes for their preparation are known in principle and the process according to the invention is not restricted to the use of particular multimetal oxide compositions. To prepare the catalytically active composition, the starting materials are typically suitable sources, known per se, of the catalytically active compositions, from which a very intimate, preferably finely divided, dry mixture is obtained and is then subjected to calcination and converted to finely divided form by grinding if appropriate. For instance, oxidic compositions are prepared, for example, from oxides themselves or from compounds which can be converted to oxides by heating, if appropriate in the presence of oxygen. Suitable starting compounds are, for example, halides, nitrates, formates, oxalates, acetates, carbonates, hydroxides, etc. The starting compounds can be mixed intimately in wet or in dry form. When it is effected in dry form, the starting compounds are appropriately used in the form of fine powder and, after mixing and compaction if appropriate, subjected to calcination. However, preference is given to effecting the intimate mixing in wet form. Typically, the starting compounds are mixed with one another in the form of an aqueous solution or suspension. Subsequently, the aqueous composition is dried and calcined after drying. Preference is given to effecting the drying operation by spray drying. The powder obtained is frequently found to be too fine for direct further processing. In these cases, it can be kneaded with addition of water. The kneaded composition obtained is subsequently subjected to calcination and then ground to give a fine oxidic active composition. The calcination conditions are known per se to those skilled in the art for the various possible oxidic active compositions. The calcination operation may itself be an exothermic or endothermic process.

Some preferred stoichiometries of multielement oxide compositions for individual gas phase reactions are detailed below merely by way of example. Multielement oxide compositions which are particularly suitable as the active composition for catalysts for the heterogeneously catalyzed partial gas phase oxidation of acrolein to acrylic acid, of methacrolein to methacrylic acid, of propene to acrolein and of tert-butanol, isobutane, isobutene or tert-butyl methyl ether to methacrolein may comprise, in addition to the elements Nb and/or W, and also Mo, V and Cu, additionally, for example, the elements Ta, Cr, Ce, Ni, Co, Fe, Mn, Zn, Sb, Bi, alkali metal (Li, Na, K, Rb, Cs), H, alkaline earth metal (Mg, Ca, Sr, Ba), Si, Al, Ti and Zr. Of course, a multielement oxide active composition used in accordance with the invention may also consist, in addition to oxygen, only of the elements Nb and/or W, and Mo, V and Cu.

Suitable active compositions for catalysts for the gas phase oxidation of acrolein to acrylic acid, of methacrolein to methacrylic acid and of propene to acrolein are particularly catalytically active multielement oxide compositions which satisfy the following general stoichiometry I:

$$Mo_{12}V_a X^1_b X^2_c X^3_d X^4_e X^5_f X^6_g O_n \qquad (I)$$

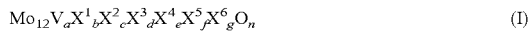

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals (Li, Na, K, Rb, Cs) and/or H,
$X^5$=one or more alkaline earth metals (Mg, Ca, Sr, Ba),
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in I other than oxygen.

The preparation of active multimetal oxides I including the calcination conditions is described, for example, by DE-A 43 35 973. DE-A 43 35 973 also discloses preferred embodiments within the active multimetal oxides 1. These include, for example, those multimetal oxides I which are embraced by the following definitions of the variables of the general formula I:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 2.5 to 5,
b=from 0.5 to 2,
c=from 0.5 to 3,
d=from 0 to 2,
e=from 0 to 0.2,
f=from 0 to 1,
g=from 0 to 15 and
n=a number which is determined by the valency and frequency of the elements in I other than oxygen.

Preference is further given to the following multielement oxide active compositions 11:

$$Mo_{12}V_a X^1_b X^2_c X^5_f X^6_g O_n \qquad (II)$$

in which the variables are each defined as follows:
$X^1$=W and/or Nb,
$X^2$=Cu and/or Ni,
$X^5$=Co and/or Sr,
$X^6$=Si and/or Al,
a=from 3 to 4.5,
b=from 1 to 1.5,
c=from 0.75 to 2.5,
f=from 0 to 0.5,
g=from 0 to 8 and
n=a number which is determined by the valency and frequency of the elements in II other than oxygen.

Preference is further given to the use of multielement oxide compositions of the general formula III $$Mo_{12}Bi_a Fe_b X^1_c X^2_d X^3_e X^4_f O_n \qquad (III)$$

in which the variables are each defined as follows:
$X^1$ nickel and/or cobalt,
$X^2$ thallium, an alkali metal and/or an alkaline earth metal,
$X^3$ phosphorus, arsenic, boron, antimony, tin, cerium, lead, niobium and/or tungsten,
$X^4$ silicon, aluminum, titanium and/or zirconium,
a from 0.5 to 5,
b from 0.01 to 3,
c from 3 to 10,
d from 0.02 to 2,
e from 0 to 5,
f from 0 to 10 and
n is a number which is determined by the valency and frequency of the elements of II other than oxygen as suitable.

The preparation of active multimetal oxides III including the calcination conditions is described by DE-A 40 23 239. Coated catalysts prepared with the active multimetal oxides III are suitable in particular for the catalytic oxidative preparation of acrolein from propene in the gas phase. The general reaction conditions for the catalytic oxidation of propene to acrolein in the gas phase can likewise be found in DE-A 40 23 239 and in DE-A 44 31 957. However the aforementioned coated catalysts of the active multimetal oxides III are also suitable for the catalytic oxidative preparation of methacrolein from tert-butanol, isobutane, isobutene or tert-butyl methyl ether in the gas phase. The general reaction conditions for this catalytic gas phase oxidation can be found, for example, in DE-A 40 23 239 and in DE-A 43 35 172.

The process according to the invention is suitable in principle for charging reactors of any design. Its advantageous properties are developed in particular in relatively long reactors (for example from 500 mm) which are charged from the upper end with utilization of gravity. The same applies to reactors which are aligned with their long side substantially vertical for the purpose of charging, but operated in another alignment (for example substantially horizontally). The reactors used in the process according to the invention preferably have a ratio of average length in vertical direction to average length in horizontal direction of at least 1, in particular at least 2 and especially at least 5. Preferred reactors are elongated hollow bodies which preferably have a substantially circular cross section.

The process according to the invention is preferably used to charge reactors which comprise at least one reactor tube. The length of the reactor tubes is preferably in a range from about 500 to 20 000 mm, more preferably of from about 1000 to 10 000 mm. The internal diameter of the reactor tubes is preferably in a range from about 5 to 100 mm, more preferably of about 10 to 50 mm. The ratio of the length of the reactor tube to its diameter is preferably about 2 to 10 000, more preferably from about 5 to 7000.

The process is particularly advantageously suitable for charging reactors which are designed in the form of tube bundle reactors (multiple catalyst tube reactors). A typical design of such reactors consists of a generally cylindrical vessel in which a multitude of tubes (a tube bundle) is accommodated in typically vertical arrangement. For use in catalytic gas phase reactions, each of these tubes (catalyst tubes) comprises a filling of a catalytically active composition or of a precursor of such a composition. Typically, the ends of the catalyst tubes are secured with sealing in tube plates and open into a hood joined to the vessel at the upper and at the lower end. Through these hoods, a gas which flows through the catalyst tubes, for example an oxygenous gas, in the course of drying and/or calcining, or the reaction gas mixture, can be fed or removed. It is possible to pass heat exchange media through the space surrounding the catalyst tubes in order to heat the catalyst tubes or remove process heat. Appropriately, tube bundle reactors have at least 5000, preferably at least 10 000 reactor tubes. In a typical embodiment, their number is, for example, from 15 000 to 30 000. Suitable heat exchange media are gaseous and liquid heating media such as steam and salt melts.

The catalyst particles generally have an average (greatest) diameter of from 1 to 40 mm, preferably from 2 to 30 mm, in particular from 3 to 20 mm. Suitable unsupported catalysts consist of a catalytically active composition which, if appropriate with use of suitable binders, is shaped by extruding, tableting or other processes to give shaped bodies such as extrudates, tablets or the like. To this end, it is possible to add to the catalytically active composition customary assistants, for example lubricants such as graphite or fatty acids (such as stearic acid), and/or shaping assistants and reinforcing agents such as fibers of glass, asbestos, silicon carbide or potassium titanate. It is also possible to add to the composition, before or after the shaping, a liquid substance or a composition comprising such a substance as described above.

The process according to the invention is preferably suitable for charging reactors with coated catalysts. Coated catalysts comprise a catalytic composition applied in coating form to a support. They may be present in the form of spheres, rings, cylinders, cubes, cuboids or other geometric bodies.

The support materials are preferably chemically inert, i.e. they substantially do not intervene in the course of the gas phase reaction which is catalyzed by the coated catalysts used. Useful materials for the particulate support (support bodies) are in particular alumina, silicon dioxide, silicates such as clay, kaolin, steatite, pumice, aluminum silicate and magnesium silicate, silicon carbide, zirconium dioxide and thorium dioxide. A suitable commercially available support is Steatit C 220 from CeramTec.

Advantageously, the surface of the support body is rough, since increased surface roughness generally results in increased adhesion strength of the applied coating to oxidic active composition. The surface roughness $R_z$ of the support body is preferably in the range from 30 or 40 to 200 µm, preferably from 30 or 40 to 100 µm (determined according to DIN 4768 sheet 1 with a "Hommel tester for DIN-ISO surface parameters" from Hommelwerke). The surface roughness mentioned is preferred especially when Steatite C 220 supports from CeramTech are used. The support materials may be porous or nonporous. The support material is preferably nonporous (total volume of the pores based on the volume of the support body <1% by volume).

In principle, any geometries of the support bodies are suitable for the process according to the invention. Their longitudinal extent is generally from 1 to 10 mm. However, preference is given to using spheres or cylinders, in particular hollow cylinders, as support bodies.

When spheres are used as support bodies, their diameter is generally from 1 to 10 mm, in particular from 3 to 8 mm.

When cylinders are used as support bodies, their length is preferably from 2 to 10 mm and their external diameter preferably from 4 to 10 mm. In the case of rings, the wall thickness is further typically from 1 to 4 mm. Particularly preferred annular support bodies have a length of from 3 to 6 mm, an external diameter of from 4 to 8 mm and a wall thickness of from 1 to 2 mm. Very particular preference is given to rings of geometry 7 mm×3 mm×4 mm (external diameter×length×internal diameter).

The thickness of the catalytically active composition or of the precursor applied to the support body is appropriately generally from 10 to 1000 µm. Especially in the case of annular support bodies, preference is given to from 10 to 500 µm, particular preference to from 100 to 500 µm and very particular preference to from 200 to 300 µm.

The catalyst particles can be prepared by known processes. Preference is given to using a binder which comprises a liquid substance as defined above and to dispensing with drying steps which lead to full or substantially full removal of the liquid substance. Partial drying may be effected, for example, by heating to a temperature of not more than 150° C., preferably not more than 120° C. For drying, a gas stream may additionally be led past the particles. The drying time is preferably not more than 60 minutes, more preferably not more than 30 minutes.

Catalyst particles which comprise a liquid substance as described above, for example in associated form, are notable for good durability with respect to mechanical stresses. This generally exceeds the mechanical durability of catalyst particles which are obtained by the same preparation process but are additionally subjected to a drying step to substantially fully remove liquid substances.

One measure of the mechanical durability of the catalyst particles prepared is the following drop test: a 20 g portion of catalyst is allowed to fall through a 3.5 m-long tube (material:

RST 37.8) with an internal diameter of 25 mm. The catalyst falls into a porcelain dish attached seamlessly to the lower end of the tube and, for the triple drop test, is removed from the dust formed in the impact and allowed to fall again through the tube. The total loss of mass after single or repeated drop test is a measure of the attrition resistance of the catalyst.

The catalyst particles prepared preferably have a weight decrease in the drop test of at most 0.8% by weight, more preferably of at most 0.7% by weight, in particular of at most 0.6% by weight. A catalyst used in accordance with the invention compared to a catalyst of the same composition but without liquid preferably has a reduction in the weight decrease in the single drop test (by a factor) of at least 0.9% by weight, more preferably at least 5% by weight, in particular at least 10% by weight. In the case of triple repetition of the drop test with the same particles, the catalyst particles prepared preferably have a weight decrease of at most 3% by weight, more preferably of at most 2.5% by weight, in particular at most 2% by weight. The weight decrease compared to a catalyst of the same composition but without liquid can preferably be decreased by (a factor of) at least 3% by weight, more preferably at least 15% by weight, in particular at least 30% by weight.

The catalyst charges obtained by the process according to the invention in the dried state have a less tightly packed, looser bed with lower bulk density. The process according to the invention provides charged reactors which have a lower pressure drop in operation than reactors which are charged with dry catalyst particles.

Irrespective of the type and composition of the catalytically active material, coated catalyst particles can be prepared in principle by contacting the support with a liquid binder and the catalytically active composition, thus applying a layer of the composition to the support, and subsequently partly removing the binder if appropriate. To prepare the catalyst particles, the catalytically active material is applied already in its finished catalytically active form, for example as the calcined mixed oxide. For the provision of the catalyst particles on the industrial scale, the process principle disclosed in DE-A-29 09 671, for example, is recommended and another liquid binder as defined above is used instead of water if appropriate. A preferred embodiment of this process variant is described in EP-A-714 700. Afterward, the support is initially moistened with the liquid binder, then a layer of active catalyst composition is adhered to the surface of the moistened support body by contacting with dry, finely divided active catalyst composition, and the liquid binder is subsequently partly removed if appropriate. In a specific embodiment, the steps of moistening the support, contacting with the catalyst composition and removing the liquid binder are repeated once or more than once until the desired layer thickness of the coated catalyst has been attained. Apart from the last repetition, the liquid binder may in each case be removed fully.

In a preferred embodiment, the support bodies to be coated are charged into a preferably inclined (the angle of inclination is generally from 30 to 90°) rotating vessel (for example rotary pan or coating drum). The rotating vessel conducts the especially spherical or cylindrical, in particular hollow cylindrical, support bodies under two metering devices arranged successively in a certain separation. The first of the two metering devices corresponds appropriately to a nozzle by which the support bodies rolling in the rotating pan are sprayed and moistened in a controlled manner with the liquid binder to be used in accordance with the invention. The second metering device is disposed outside the atomization cone of the sprayed liquid binder and serves to supply the finely divided active composition (for example via an agitated channel or a powder screw). The support bodies which have been moistened in a controlled manner take up the powder supplied, which is compressed by the rolling motion to a continuous coating on the outer surface of the cylindrical or spherical support body. (In the inner circle of a hollow cylindrical support body, such a compressive motion does not take place, which is why it remains substantially uncoated. However, this can be prevented, for example, by employing a slurry coating process, for example using an Ultracoater from Aeromatic Fielder, Switzerland).

If required, the support body basically coated in this way, in the course of the subsequent rotation, again passes through the spray nozzle, and is moistened in a controlled manner, in order, in the course of the further rotation, to be able to take up a further layer of finely divided active composition, etc. (intermediate drying is generally not required). A particular advantage of the above-described embodiment consists in the possibility of preparing coated catalysts having, in layer form, coatings consisting of two or more different active compositions in one working step.

An advantage in the above-described embodiment for preparing the catalyst particles to be charged into the reactor is that the moistening of the surface of the support body to be coated and of the resulting coated catalysts can be undertaken in a controlled manner. Appropriately, the support surface is moistened in such a way that, although it comprises adsorbed liquid binder, no liquid phase as such appears visually on the support surface or on the applied layers. In this embodiment, it is possible to prepare catalyst particles which comprise a precisely determined amount of liquid associated binder. The maximum amount of liquid corresponds to the maximum degree of saturation of the catalyst particles. For the process according to the invention, it is of course also possible, as already mentioned, to prepare the catalyst particles by contacting catalyst particles obtained by any process with a liquid substance and subsequently using them to charge the reactor.

The reactor and the catalyst particles in the course of charging preferably have a temperature of at most 50° C., more preferably of at most 40° C. and in particular of at most 30° C. In a preferred embodiment, the reactor is charged at the particular ambient temperature.

The reactor is charged with the catalyst particles generally by introducing it into an orifice at the upper end of the reactor and into the reactor under the action of gravity. The catalyst particles are preferably charged into the reactor at a substantially constant rate, in particular with the aid of suitable charging machines. In the charging of tube bundle reactors, preference is given to using charging machines which are suitable for simultaneously charging several tubes. These have, for example, a charging funnel with a plurality of chambers from which the catalyst particles are expelled onto an inclined agitated channel. When the agitated channel is set into vibration, the catalyst particles slide uniformly over the channel and fall through cutouts in the channel into the tubes below. Suitable apparatuses for charging catalyst particles into tubular reactors are described in DE-A 25 11 411, DE-A-28 49 664, EP-A-041 144, DE-A-199 34 324 and DE-A-102 50 022. Reference is made here to the disclosure content of these documents. A particularly advantageous use of the apparatus described in DE-A-1 99 34 324 is for charging bulk material into tubes which have a number of stock vessels, which take up the bulk material, and conveying channels below the stock vessels, in which the bulk material is set into vibration and conveyed to a discharge point, the amount conveyed into the conveying channel being meterable. Advantageously, it is also possible to use a loading apparatus which is described in DE-A-102 50 022 and consists of a multitude of loading elements and is therefore particularly suitable for tube bundle reactors having a multitude of reactor tubes.

The process according to the invention preferably enables charging aids in the reactor which lead to slowing of the speed at which the catalyst particles fall to be dispensed with.

In a preferred embodiment, the charged reactor, before it is used in catalytic gas phase reactions, is subjected initially to a treatment to remove at least a portion of the liquid substance and of further volatile constituents if appropriate, for example further binder components. This may be effected, for example, by heating to an elevated temperature (frequently from 50 to 220° C.) and/or passing through a gas stream. In the simplest case, the liquid substance and further components if appropriate are removed by the action of hot gases of the appropriate temperature. The gas used is generally an oxygenous gas, in particular atmospheric oxygen. The temperature should generally not be above the calcination temperature employed to prepare the oxidic active composition. In general, such a heating of the reactor to elevated temperatures below the calcination temperature is sufficient, since water and most organic solvents and also numerous organic binder components decompose over the oxidic compositions used as catalysts and in the presence of atmospheric oxygen to give gaseous constituents such as formic acid, acetic acid, $H_2O$, $CO_2$ or CO. It is thus generally possible to carry out the thermal treatment to remove the liquid substance and any further components in such a way that the offgas stream can be passed out of the reactor without aftertreatment into the atmosphere.

In a typical embodiment, the reactor charged by the process according to the invention is used in a production plant, for example for the catalytic oxidation of acrolein to acrylic acid in the gas phase. Such production plants consist generally of one or more production lines connected in parallel. Each production line may itself be formed from one or more reactors connected in series. The products of the catalytic gas phase reaction of each reaction line may be worked up separately or together, for example by customary separation and purification processes known to those skilled in the art. For effective utilization of the workup plants, for example of the distillation columns customary therefor, the product streams from two, three or more than three production lines are in many cases sent to a common workup. The process according to the invention is suitable in a particularly advantageous manner for the effective operation of a production plant composed of two, three or more than three parallel production lines, in which case only one individual line is shut down in each case for the exchange, required after a certain catalyst onstream time, of the catalyst charge, and the production continues in the remaining lines. The rapid and nevertheless uniform charging of the reactors with prevention of catalyst fracture and/or attrition which is possible by the process according to the invention allows the production shutdown to be restricted to a minimum.

In a suitable embodiment, the freshly charged reactor or the reactors, connected in series, of a production line is/are initially heated with a heated gas, generally air, which is conducted through the reactor to remove the liquid substance and any further binder components, and the volatile components are simultaneously removed from the reactor. The amount of gas used is, for example, in a range from about 0.8 to 1.2 $m^3$ (STP)/h tube. The outgoing air leaving the reactor, as detailed above, can generally be passed into the atmosphere. For the thermal treatment of the reactor, preference is given to using a temperature gradient so as not to expose the reactor and the charge to excessive stress as a result of brief, strong heating.

The heating rate is preferably not more than 10° C. per hour. For example, the reactor may initially be heated with heated air at a temperature below 100° C., for example in a range from 50 to 90° C. In general, the temperature differential between reactor inlet and reactor outlet (measured in each case in the gas inlet and gas outlet) should be not more than 120° C., preferably not more than 90° C. The gases can be heated using customary apparatus, for example using a gas compressor or using steam-fed heat exchangers. When the reactor has attained a sufficient temperature, further additional heating may be effected using the heat exchange media which typically surround the catalyst tubes, for example salt melts. This heating may be effected electrically, for example using the heating element introduced into the heating medium. In the course of the further heating, another gas, preferably oxygen-depleted air, may also flow through the reactor instead of air. In order to ensure full removal of the liquid substance and of any further binder components, the reactor is heated to a sufficiently high temperature, for instance from 160 to 220° C., for a sufficiently long time, for instance from 12 to 72 hours. As soon as substantially no liquid substances or binder components or decomposition products thereof can be detected at the outlet of the reactor, the reactor or the production line can be reintegrated into the reaction circuit, heated to the necessary starting temperature and charged with reactant gas.

The invention further provides the reactors which are charged with catalyst particles and are obtainable by the process described above.

Owing to their above-described advantageous packing properties, these reactors are outstandingly suitable for carrying out catalytic gas phase reactions.

The invention also provides for the use of an inventive reactor for carrying out catalytic gas phase reactions, in particular for preparing unsaturated aliphatic carboxylic acids or aldehydes by gas phase oxidation of aldehydes, alkanes or alkenes; for preparing nitriles by ammoxidation of alkanes or alkenes; for preparing aromatic carboxylic acids or anhydrides by gas phase oxidation of aromatic hydrocarbons, for epoxidations and for hydrogenations.

In a preferred embodiment, inventive reactors are used, after the charging, to prepare acrylic acid by catalyzed oxidation of acrolein in the gas phase. The reaction is effected at least partly, in particular fully, in a reactor as defined above. Multimetal oxides suitable for the catalytic oxidative preparation of acrylic acid from acrolein in the gas phase have already been mentioned at the outset and are common knowledge. The reaction conditions for the catalytic oxidation of acrolein to acrylic acid in the gas phase are described, for example, in DE-A-43 35 973. The inventive catalysts are also suitable for use for preparing acrylic acid in a multiple catalyst tube fixed bed reactor through whose space surrounding the catalyst tubes is passed a heat exchange medium circulation system, as described in DE-A-44 31 949.

To prepare acrylic acid by catalytic oxidation of acrolein in the gas phase, it is possible to use acrolein which has itself been obtained by catalytic gas phase partial oxidation of propene. It is also possible to this end to use a reactor charged in accordance with the invention. In general, the acrolein-containing reaction gases of this propene oxidation may be used without further purification to prepare acrylic acid. To this end, a cooling of the reaction gases between the reaction stages may be carried out if appropriate.

The oxidizing agent used for the oxidation of acrolein to acrylic acid (and also of propene to acrolein) is preferably oxygen, appropriately diluted with inert gases, for example in the form of air or preferably of what is known as lean air (having a lower oxygen content than air)). Suitable oxidizing agents are also gases comprising oxygen in bound form such as $N_2O$. Suitable diluent gases are, for example, $N_2$, $CO_2$, hydrocarbons, recycled reaction offgases from the acrylic acid or acrolein preparation and/or steam. In a suitable embodiment, for acrolein partial oxidation, an acrolein:oxygen:steam:inert gas volume ratio of 1:(1-3): (0-20):(3-30), preferably 1:(1-3):(0.5-10):(7-18), is established. The reaction pressure is generally from about 1 to 3 bar, and the overall superficial velocity is preferably from 1000 to 4000 l (STP)/ l/h. The reaction temperature is typically in a range from about 230 to 330° C. In a suitable embodiment, acrylic acid is prepared by catalytic oxidation in the gas phase in a production plant composed of one or more production lines as described above. It is then possible to reintegrate a reactor which has been charged by the process according to the invention and baked out in a hot air stream into the production plant. To this end, it may be necessary to briefly interrupt production in the remaining lines. In the integration into production, the newly charged production line is reconnected on the gas side to the workup apparatus, the air stream is adjusted to the oxygen:inert gas ratio used for acrylic acid preparation and acrolein is subsequently mixed into the gas stream flowing into the reactor.

The catalysts charged by the process according to the invention are suitable in particular also for the catalytic oxidative preparation of acrolein from propene in the gas phase. The general reaction conditions for the catalytic oxidation of propene to acrolein in the gas phase can be found, for example, in DE-A-40 23 239 and in DE-A-44 31 957, to which reference is made here.

The catalysts charged by the process according to the invention are also suitable for the catalytic oxidative preparation of methacrolein from tert-butanol, isobutanol, isobutene or tert-butyl methyl ether in the gas phase. The general reaction conditions for this catalytic gas phase oxidation can be found, for example, in DE-A-40 23 239 and in DE-A-43 35 172.

The catalysts charged by the process according to the invention are also suitable for the partial oxidation of aromatic hydrocarbons to carboxylic acids and/or carboxylic anhydrides. Aromatic hydrocarbons which can be used as reactants are, for example, benzene, toluene, the xylene isomers, naphthalene, etc. In this oxidation, for example, benzoic acid, maleic anhydride, phthalic anhydride, isophthalic acid, terephthalic acid or pyromellitic anhydride are obtained. Particularly important on the industrial scale is the gas phase partial oxidation of o-xylene to phthalic anhydride.

For the gas phase oxidation of aromatic hydrocarbons to carboxylic acids and/or carboxylic anhydrides, preference is given to using catalysts which comprise, in their catalytically active composition, titanium dioxide, preferably in the anatase modification, oxidic compounds of vanadium, in particular vanadium pentoxide ($V_2O_5$), and oxidic promoters if appropriate, for example based on alkali metals, alkaline earth metal, TI, Al, Zr, Fe, Ni, Co, Mn, Sn, Ag, Cu, Cr, Mo, W, Ir, Ta, Ni, As, Ce and/or P. For the gas phase oxidation of aromatic hydrocarbons, preference is given to using coated catalysts. Suitable catalyst compositions and processes for their preparation are described, for example, in DE-A-25 46 268, EP-A-286 448, DE-A-25 47 624, EP-A-163 231, DE-A-28 30 765 and WO 98/37967.

For the gas phase oxidation, a reaction gas comprising molecular oxygen is used. The reaction gases may comprise, in addition to oxygen, also suitable reaction moderators and/ or diluents, such as steam, carbon dioxide and/or nitrogen. The reaction gas generally comprises preferably from 1 to 100 mol %, more preferably from 2 to 50 mol %, in particular from 10 to 30 mol %, of oxygen. Additionally, the gas may comprise up to 30 mol %, preferably up to 10 mol %, of steam, and from 0 to 50 mol %, preferably from 0 to 1 mol %, of carbon dioxide. The difference up to 100 mol % may be nitrogen. The reaction gas fed to the reactor comprises, for example, from 5 g to 120 g per $m^3$ (STP) of gas, preferably from 60 to 120 g/$m^3$ (STP) of gas and in particular from 80 to 115 g/$m^3$ (STP) of gas, of the aromatic hydrocarbon to be oxidized.

The reaction temperature is generally from 300 to 450° C., preferably from 320 to 420° C. and in particular from 340 to 400° C. Typically, the reaction is carried out at an elevated pressure of generally from 0.1 to 2.5 bar, preferably from 0.3 to 1.5 bar. The superficial velocity is generally from 750 to 5000 $h^{-1}$.

The gas phase oxidation may be carried out at a uniform reaction temperature or in a reactor with division into temperature zones. To this end, two or more than two zones of the catalyst bed disposed in the reaction tube are thermostated to different reaction temperatures. To this end, suitable reactors are, for example, those having separate salt baths, as described in DE-A-22 01 528 or DE-A-28 30 765. When the reaction is carried out in two reaction zones, as described in DE-A-40 13 051, the reaction zone disposed toward the gas inlet of the reaction gas, which generally comprises from 30 to 80% by volume of the total catalyst volume, is thermostated to a reaction temperature which is higher than the reaction zone disposed toward the gas outlet by from 1 to 20° C., preferably by from 1 to 10° C. and in particular by from 2 to 8° C. Such an operating mode is referred to as two-zone or multizone structuring of the reactor.

It is possible to proceed in a similar manner in the oxidation of toluene to benzoic acid, in which case a mixture of unconverted toluene, benzoic acid and benzaldehyde is initially formed. Alternatively, it is also possible if desired to isolate the benzaldehyde by-product.

The catalyst filling carried out by the process according to the invention is suitable especially also for the performance of a catalyst change according to WO 2004009525 A1. On completion of a partial change, the liquid substance and, if appropriate, further binder are removed in accordance with the process according to the present invention described above without there being any impairment of the quality of the remaining catalyst bed already present in the reactor and unaffected by the partial change.

The invention is illustrated in detail with reference to the non-restrictive examples which follow.

EXAMPLES (I) Preparation of Coated Catalysts

Example 1

Comparison

A precursor composition for preparing a multielement oxide composition of the stoichiometry $Mo_{12}V_3W_{1.2}Cu_{2.4}O_x$ was prepared as described in Example A) of DE-A-103 60 057 and a catalytic active composition was obtained therefrom by thermal treatment in a rotary oven apparatus as described in Example B) of this document. The thus obtained catalytically active material was ground by means of a biplex crossflow classifying mill (BQ 500) (from Hosokawa-Alpine, Augsburg) to give a fine powder of which 50% of the powder particles passed a sieve of mesh width from 1 to 10 μm and whose proportion of particles having a longitudinal extent above 50 μm was less than 1%.

28 kg of annular support bodies (external diameter 7 mm, length 3 mm, internal diameter 4 mm, steatite, having a surface roughness $R_z$ of 45 μm and having a total pore volume, based on the volume of the support bodies, of <1% by volume, manufacturer Hoechst Ceramtec, Germany) was charged into a coating tank (angle of inclination 90°; Hicoater from Lödige, Germany) of capacity 200 l. Subsequently, the coating tank was set into rotation at 16 rpm. Using a nozzle (Schlick type, 0.5 mm, 90°), 2000 g of a solution consisting of 75% by weight of water and 25% by weight of glycerol were sprayed onto the support bodies within 25 min. At the same time, 10.35 kg of the catalytically active material were metered continuously using an agitated channel outside the spray cone of the atomizer nozzle within the same period. During the coating, the powder supplied was taken up fully on the surface of the support bodies; agglomeration of the finely divided oxidic active composition was not observed. On completion of addition of powder and binder, air at 110° C. was blown into the coating tank at a rotation rate of 2 rpm for 20 min. Subsequently, drying was effected under air at 250° C. in a standing bed (tray oven) for 2 h.

Example 2

Inventive

The procedure of Example 1 was repeated, except that the drying at 250° C. in a tray oven for 2 h was dispensed with.

Example 3

Comparison

A precursor composition for preparing a multielement oxide composition of the stoichiometry $(Mo_{12}V_{3.46}W_{1.39})_{0.87}(CuMo_{0.5}W_{0.5}O_4)_{0.4}(CuSb_2O_6)_{0.4}$ was prepared as in Example 5.) of DE-A-103 60 058 and a catalytically active composition was prepared therefrom by thermal treatment in a rotary oven apparatus. The thus obtained catalytically active material was ground by means of a biplex crossflow classifying mill (BQ 500) (from Hosokawa-Alpine, Augsburg) to give a fine powder of which 50% of the powder particles passed a sieve of mesh width from 1 to 10 μm and whose proportion of particles having a longitudinal extent above 50 μm was less than 1%. This was used to prepare a coated catalyst as described above in comparative example 1.

Example 4

Inventive

The procedure of Example 3 was repeated, except that the drying at 250° C. in a tray oven for 2 h was dispensed with.

II. Performance Properties a) Drop Test 20 g of catalyst were allowed to fall through a 3.5 m-long tube with internal diameter of 25 mm. The catalyst falls into a dish directly below the tube, is removed from the dust formed on impact and is again allowed to fall through the tube. The total loss of mass after being allowed to fall from one to three times is a measure of the attrition resistance of the catalyst. The results are listed in Table 1 below.

TABLE 1

| Drop test Number | Catalyst from Example No. Loss of active composition mass [% by weight] | | | |
|---|---|---|---|---|
| | 1 comparison | 2 inventive | 3 comparison | 4 inventive |
| 1 | 0.93 | 0.56 | 0.90 | 0.59 |
| 2 | 2.99 | 1.33 | 2.44 | 1.19 |
| 3 | 4.35 | 1.99 | 3.29 | 1.89 |

What is claimed is:

1. A process for charging a reactor with catalyst particles which have a catalytically active multielement oxide composition at least on its surface, the process comprising:
   providing catalyst particles comprising a substance which is liquid at 20° C. and 1 atm, and having a content of the liquid substance from 0.05% to 10% by weight,
   charging the catalyst particles into the reactor, and
   removing the liquid substance from the charged reactor.

2. The process according to claim 1, wherein the catalyst particles are selected from shaped bodies which comprise at least one catalytically active multielement oxide composition and particles which comprise at least one catalytically active multielement oxide composition applied in a coating form to a support.

3. The process according to claim 1, wherein the liquid substance is selected from water and organic compounds which have a boiling point at 1 atm of more than 100° C.

4. The process according to claim 1, wherein the reactor comprises at least one reactor tube.

5. The process according to claim 4, wherein the reactor tube has a length of from 500 mm to 20,000 mm.

6. The process according to claim 4, wherein the reactor tube has an internal diameter of from 5 to 100 mm.

7. The process according to claim 6, wherein the ratio of the length of the reactor tube to its diameter is in a range from 2 to 10,000.

8. The process according to claim 4, wherein the reactor is designed as a tube bundle reactor, which is a multiple catalyst tube reactor.

9. The process according to claim 8, wherein the tube bundle reactor has at least 5000 reactor tubes.

10. The process according to claim 1, wherein the catalyst particles have the content of the liquid substance of from 0.1 to 5% by weight, based on the total weight of the catalyst particles.

11. The process according to claim 1, wherein the catalyst particles have a weight decrease of at most 0.8% by weight in a drop test, wherein a 20 g portion of a catalyst, a drop tube internal diameter of 25 mm, and the length of 3,500 mm are used.

12. The process according to claim 1, wherein binder-containing catalyst particles, in a triple repetition of a drop test with the same particles, have a weight decrease of at most 3% by weight.

13. The process according to claim 1, wherein binder-containing catalyst particles have an average external diameter of from 1 to 40 mm.

14. The process according to claim 1, wherein the catalyst particles are provided by contacting a support with a binder comprising a substance which is liquid at 20° C. and 1 atm and the catalytically active composition, and, optionally, the binder is subsequently partly removed.

15. The process according to claim 14, wherein the support is initially moistened with the binder comprising the liquid substance, then a layer of the catalytically active composition is adhered to the surface of the moistened support by contacting with the dry, finely divided catalytically active composition, and, optionally, the liquid binder is subsequently partly removed.

16. The process according to claim 15, wherein the moistening the support, contacting with the catalytically active composition and removing the liquid binder are repeated at least once, and the liquid binder is optionally removed fully except for the last repetition.

17. The process according to claim 14, wherein the support is a support body having a surface roughness Rz of from 40 to 100 μm.

18. The process according to claim 17, in which the support body has a total volume of pores, based on the volume of the support body, of at most 1% by volume.

19. The process according to claim 1, wherein the reactor and the catalyst particles, in the course of charging of the reactor, have a temperature of at most 50° C.

20. The process according to claim 1, wherein the catalyst particles are charged into the reactor by introducing them into an orifice at the upper end of the reactor and under the action of gravity.

21. The process according to claim 20, wherein no charging aid which leads to a slowing of the speed at which the catalyst particles fall is present in the reactor.

22. The process according to claim 1, wherein the charged reactor is subsequently used for a catalytic oxidative preparation of acrylic acid from acrolein in a gas phase.

23. The process according to claim 1, wherein the charged reactor is subsequently used for a catalytic oxidative preparation of methacrylic acid from methacrolein in a gas phase.

24. The process according to claim 1, wherein the charged reactor is subsequently used for a catalytic oxidative preparation of acrolein from propene in a gas phase.

25. The process according to claim 1, wherein the charged reactor is subsequently used to prepare carboxylic acids and/or carboxylic anhydrides by a catalytic oxidation of at least one aromatic hydrocarbon selected from the group consisting of benzene, toluene, xylene isomer, and naphthalene, in a gas phase.

26. A process for preparing acrylic acid by a gas phase catalyzed oxidation of acrolein, wherein the preparing is conducted at least partly in the reactor charged according to claim 1.

27. A process for preparing unsaturated aliphatic carboxylic acids or aldehydes by a gas phase oxidation of aldehydes, alkanes or alkenes; nitriles by ammoxidation of alkanes or alkenes; for preparing aromatic carboxylic acids or anhydrides by a gas phase oxidation of at least one aromatic hydrocarbon selected from the group consisting of benzene, toluene, xylene isomer, and naphthalene, for epoxidations, or for hydrogenations by carrying out catalytic gas phase reactions in the reactor charged according to claim 1.

28. The process according to claim 25, wherein the xylene isomer is o-xylene.

29. The process according to claim 27, wherein the xylene isomer is o-xylene.

* * * * *